United States Patent [19]

Schwartz

[11] Patent Number: 4,828,984
[45] Date of Patent: May 9, 1989

[54] COMPOSITION, SYNTHESIS AND USE OF SIMULATED CELLS

[75] Inventor: Abraham Schwartz, Durham, N.C.

[73] Assignee: Flow Cytometry Standards Corporation, Research Triangle Park, N.C.

[21] Appl. No.: 850,746

[22] Filed: Apr. 11, 1986

[51] Int. Cl.⁴ ............... G01N 33/533; G01N 33/546; G01N 33/547; G01N 33/554
[52] U.S. Cl. ..................... 435/7; 436/519; 436/533; 436/534; 436/548; 436/800
[58] Field of Search ............ 435/180, 181, 7; 436/501, 519, 529, 533, 534, 800, 548; 530/815, 816

[56] References Cited

U.S. PATENT DOCUMENTS

| | | | |
|---|---|---|---|
| 4,035,316 | 7/1977 | Yen et al. | 260/2.5 B |
| 4,157,323 | 6/1979 | Yen et al. | 260/29.7 M |
| 4,210,723 | 7/1980 | Dorman et al. | 436/534 |
| 4,247,434 | 1/1981 | Lovelace | 260/29.6 RB |
| 4,254,096 | 3/1981 | Monthony et al. | 436/534 |
| 4,336,173 | 6/1982 | Ugelstad | 523/205 |
| 4,438,239 | 3/1984 | Rembaum et al. | 525/54.1 |
| 4,511,662 | 4/1985 | Baran et al. | 436/531 |
| 4,552,633 | 11/1985 | Kumakura et al. | 435/180 |
| 4,605,630 | 8/1986 | Kung et al. | 436/800 |
| 4,656,144 | 4/1987 | Mosaka et al. | 436/534 |
| 4,665,020 | 5/1987 | Saunders | 436/533 |

OTHER PUBLICATIONS

V. Ghetie et al., *Meth. Enzymol.* 108, 405–413, 1984.
R. C. Nairn *Fluorescent Protein Tracing*, 4th Edition, Churchill Livingston, Edinburgh, 1976, pp. 40–46.
*Nature Directory of Biologicals*, 1983, p. 218.
Pharmacia Fine Chemicals, *Ficoll-Paque ® For In Vitro Isolation of Lymphocytes*, 1983, p. 3.
NASA TM78132 entitled "Large-Size Monidisperse Latexes As A Commercial Space Product".

Primary Examiner—Sidney Marantz
Assistant Examiner—David A. Saunders
Attorney, Agent, or Firm—Steven J. Hultquist

[57] ABSTRACT

The synthesis, composition and use of particles exemplified by microbeads of uniform size and character, with covalently bound biological molecules for biological simulation is disclosed.

10 Claims, 3 Drawing Sheets

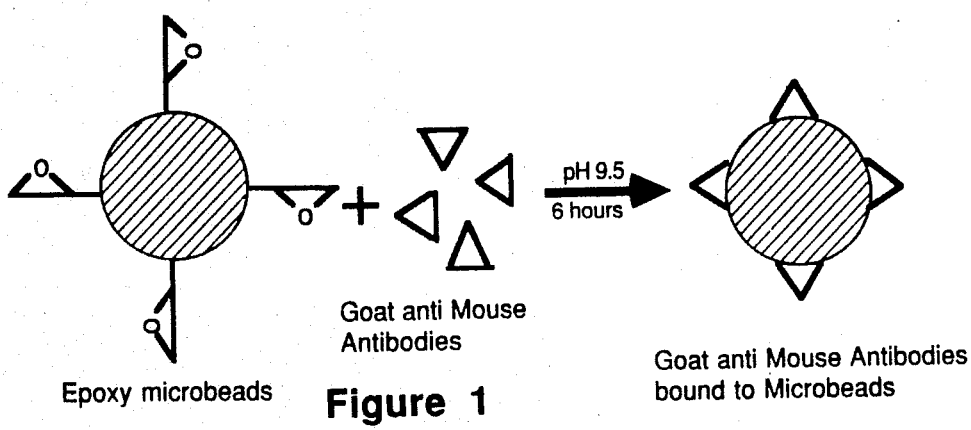
Epoxy microbeads    Figure 1    Goat anti Mouse Antibodies bound to Microbeads
Goat anti Mouse Antibodies
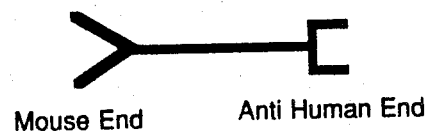
Mouse End    Anti Human End
Figure 2
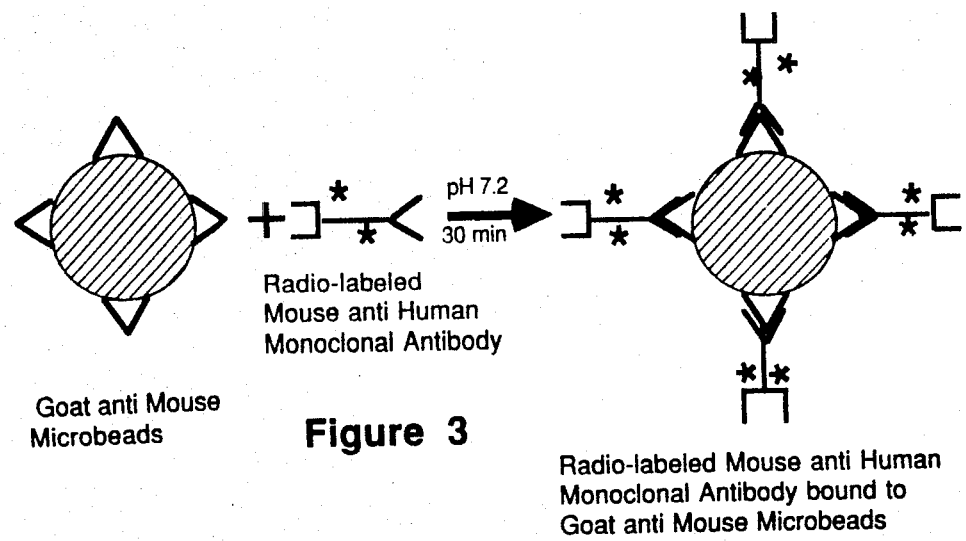
Goat anti Mouse Microbeads    Figure 3    Radio-labeled Mouse anti Human Monoclonal Antibody bound to Goat anti Mouse Microbeads
Radio-labeled Mouse anti Human Monoclonal Antibody Goat anti Mouse Microbeads Fluorescent Mouse anti Human monoclonal antibody bound to Goat anti Mouse Microbeads

COMPOSITION, SYNTHESIS AND USE OF SIMULATED CELLS

TECHNICAL FIELD

The invention relates to the composition, synthesis and use of uniform particles to which functional biological molecules are covalently bound. More specifically, the invention relates to such particles as they may simulate biological cells with respect to their physical and biological properties and functions.

BACKGROUND ART

It is recognized that particles are available to which biological molecules may be attached. U.S. Pat. No. 4,438,239 describes microbeads between 100 and 2000 angstroms in diameter containing active aldehydes which form conjugates with proteins and enzymes. U.S. Pat. No. 4,035,316 describes microbeads less than 3 microns in diameter to which lectins or antibodies may be bound for use in cell separation. U.S. Pat. Nos. 4,157,323 and 4,170,685 describe impregnated functional microbeads which can be covalently bound to antibodies and used to separate cells. The described microbeads are not suitable for simulating biological cells since they are smaller than biological cells which range generally from 7–15 microns in diameter. Moreover, the described microbeads are not highly uniform and have coefficients of variation greater than five percent (5%) in diameter. More specifically, so far as applicant is aware no one has heretofore realized the possibility of covalently binding functional biological molecules to uniform microbeads for biological cell simulation.

Recently, larger highly uniform microbeads with coefficients of variation of one percent (1%) in diameter have been synthesized both in the laboratory and in outer space. Such microbeads are described in NASA publication TM78132 "Large-size Monodesperse Latexes as Commercial Space Product", in U.S. Pat. Nos. 4,247,434 and in 4,336,173. Improvements to the method described in U.S. Pat. No. 4,336,173 are described in applicant's copending applications Ser. No. 685,464 entitled "Calibration Method for Flow Cytometry using Fluorescent Microbeads and Synthesis Thereof" and Ser. No. 805,654 entitled "Fluorescent Calibration Microbeads Simulating Stained Cells". None of these larger, uniform microbeads have been described or recognized as being useful for covalently binding antibodies or enzymes in cell simulation. However, the present invention recognizes that the microbeads described in applicant's copending applications, although used as fluorescent standards for flow cytometry and fluorescence microscopy, are capable of binding proteins for biological cell simulation because of functional groups introduced on the surface. Several examples are described in applicant's copending applications of protein binding by allowing the epoxy groups on the microbead surface to react with the primary amines of protein such as avidine and those associated with phycoerythrins.

In one aspect, the simulated cells of the invention address a method of screening the specificity of fluorescent antibodies and determining the number of fluorescent dye molecules which are conjugated to antibody molecules. In another aspect, the simulated cells of the invention are recognized as having potential uses in enzyme kinetics and chelation studies. Background with respect to these aspects of the invention is next described.

One known method for screening the specificity of antibodies has been to use diffusion-precipitation techniques where different concentrations of the antigen and antibody are diffused towards each other in gels and the degree of specificity being determined by finding the lowest concentration that allows the antigen and antibody to form a visible precipitate. Another method for screening antibodies is to use an inhibition test as in hemoagglutination and ELISA (Enzyme-Linked Immunosorbent Assay) testing. Here the antibody to be screened, e.g., a mouse IgM monoclonal, is reacted with a specific antigen immobilized onto a substrate, e.g. rabbit anti mouse IgM antibody on nitro cellulose paper. Then a fluorescenated or radioactive antibody, e.g., goat anti rabbit antibody, is exposed to the surface binding the mouse IgM antibody. If no goat anti rabbit antibodies bind to the surface as determined by fluorescence or radioactivity, then all binding sites are known to be specifically tied up by the mouse IgM antibody, proving that the mouse IgM antibody is very specific. Although this methodology is common, there is no known suitable surface which can be used in conjunction with a flow cytometer for such determination with respect to size and uniformity. More specifically, the art has not provided a substrate in suspension and of the type provided by the present invention exhibiting surface characteristics and a size comparable to biological cells suited to flow cytometry techniques.

One of the important aspects of immunology and cell biology is determining the number and density of antibody binding sites on a cell. At present this determination is both difficult and subject to gross errors without careful considerations of correction factors. For example, in using fluorescence to determine this number, the key is to first determine the number of fluorescent molecules, e.g., Fluorescein Isothiocyanate, designated as FITC, which have been conjugated to an antibody molecule. This determination is commonly carried out by measuring the absorption of a solution of the antibody at 365 nm to determine the antibody concentration and then again at 490 nm (with some correction factors for the absorption at 365 nm) to determine the fluorescent dye molecule concentration. By dividing the number of fluorescent dye molecules by the number of antibody molecules, one determines the number of dye molecules per antibody molecule, commonly referred to as the F/P ratio. However, as pointed out in the technical brochure "Quantitative Fluorescein Microbead Standards", published by Flow Cytometry Standards Corporation, this F/P ratio determined by absorption may be useless when working with fluorescence because it is well recognized that when dye molecules, e.g., FITC, are close together, their fluorescence may be quenched by each other resulting in less of a fluorescence signal than anticipated. Therefore, it is necessary to measure the effective fluorescence of the dye on the antibodies in terms of equivalent soluble dye molecules. The referred-to technical brochure describes how to do this by first measuring the fluorescence in a fluorometer, e.g., for FITC; excitation at 488 nm, emission at 520 nm and then the concentration of the antibody by absorption at 365 nm as before. The problem with this method is that it requires a fluorometer and calibration plots for the absorption and the fluorescence measurements.

DISCLOSURE OF INVENTION

The present invention is based on the composition synthesis and use of highly uniform microbeads to which specific biological molecules, such as, but not limited to, antibodies, lectins, enzymes, and antigenic proteins, have been covalently bound and the subsequent calibration of the number of binding or active sites of these biological molecules per microbead. The physical and biological properties of the protein bound microbeads are such that they may act as uniform particles simulating biological cells. Such a model cell, for example, can be used to screen fluorescent antibodies by allowing an antigen bound to the microbeads to react directly with test antibodies and measuring the degree of binding with a flow cytometer. Similarly, the model cell of the invention enables the effective fluorescence of an antibody to be determined by first determining the number of available binding sites with radiolabeled antibodies on a sample of the protein bound microbeads and then determining the fluorescence of another sample of the protein microbeads after they have been reacted with the fluorescent antibody, in terms of equivalent soluble fluorescent molecules per microbead. Dividing the number of effective fluorescent molecules per microbead by the number of antibody binding sites per microbead, assuming complete saturation of available binding sites, will yield the effective fluorescence of the antibody.

While not described, the invention simulated cell is recognized as being applicable to enzyme kinetics. At present, it is very difficult to determine the efficiency of an enzyme because one must determine both the actual concentration and the effective concentration of the enzyme. From examples presented to support use of the invention's simulated cells, it is also recognized that with the invention, it becomes possible to determine both concentrations on uniform particles as well as to be able to very precisely control the amount of enzyme introduced into a system by controlling the number of the invention microbeads. Moreover, the enzyme immobilized on the invention microbeads has the advantage of being easily removed from the reaction by centrifugation to stop the reaction.

BRIEF DESCRIPTION OF THE DRAWINGS

FIG. 1 schematically illustrates binding goat anti mouse antibodies to relatively large uniform size microbeads according to the invention.

FIG. 2 is a schematic diagram of a mouse anti human monoclonal antibody.

FIG. 3 schematically illustrates reacting the goat anti mouse antibody bound microbeads of FIG. 1 with an excess of radiolabeled mouse anti human monoclonal antibodies to achieve radiolabeled mouse anti human monoclonal antibodies on goat anti mouse antibodies according to the invention.

BEST MODE FOR CARRYING OUT THE INVENTION

An initial step in practicing the invention is to make available highly uniform microbeads, made as previously referred to and as later explained in more detail. Assuming such microbeads are available, there is illustrated by way of example in FIGS. 1-3 the overall method of the invention aimed at calibrating the antibody microbeads in the sense of determining the number of available active sites on each microbead. Making reference initially to FIG. 1, it will be noted that epoxy surfaced microbeads, typically spherical in form, are combined with commercially-available, affinity-purified goat anti mouse antibodies and reacted at an indicated pH of 9.5 for a time of six hours to produce goat anti mouse microbeads with covalently immobilized affinity-purified goat anti mouse antibodies on the surface of the microbeads.

Using FIG. 2 for a reference for the basic diagram of a mouse anti human antibody, the next step in calibrating the average number of available active sites on the goat anti mouse microbeads is accomplished by allowing the goat anti mouse microbeads to react with an excess of radiolabeled mouse anti human monoclonal antibodies under the conditions of pH 7.2 and time of thirty minutes as indicated in FIG. 3. Following such reaction, the unbound radiolabeled mouse anti human monoclonal antibodies are washed away to leave the microbeads and radiolabeled mouse anti human monoclonal antibodies on the goat anti mouse antibodies as further illustrated in FIG. 3.

Following the FIG. 3 procedure a determination is next made of how many mouse anti human monoclonal antibodies are attached to the goat anti mouse microbeads. This step, later explained in more detail by way of example, is accomplished by knowing how many radioactive units represent one mouse anti human monoclonal antibody. The number of mouse anti human monoclonal antibodies thus represents the number of available active sites on each microbead.

Figure 4:
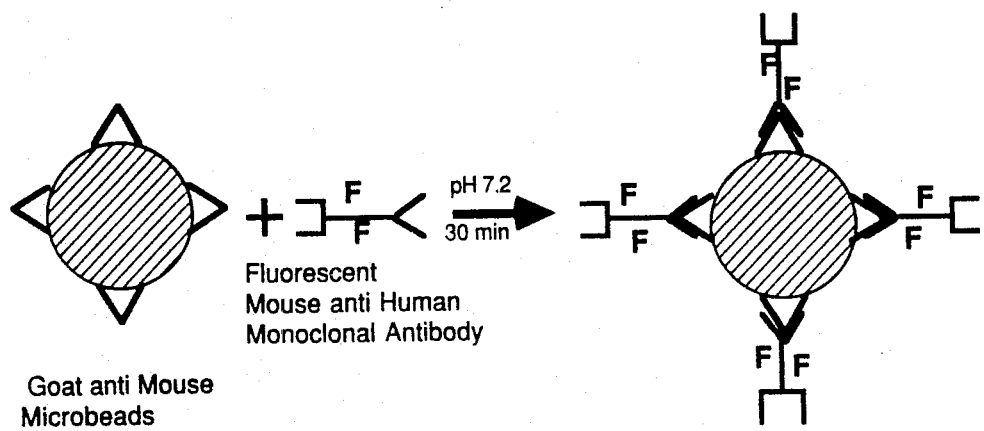
FIG. 4 schematically illustrates reacting goat anti mouse antibody bound microbeads with an excess of fluorescenated mouse anti human monoclonal antibodies to achieve microbeads with fluorescent mouse anti human monoclonal antibodies attached to goat anti mouse antibodies according to the invention.
Figure 5:
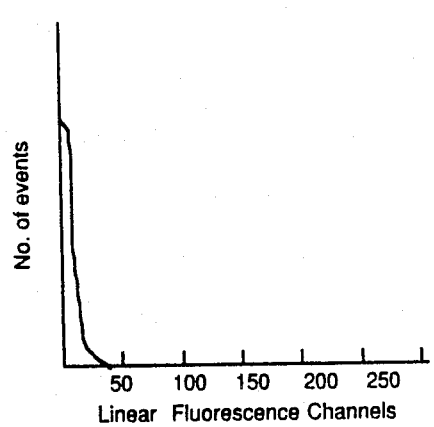
FIG. 5 illustrates the relatively low fluorescence of goat anti mouse bound microbeads, the X axis representing linear fluorescent channels and the Y axis the number of events, the curve position being generally independent of such number.
Figure 6:
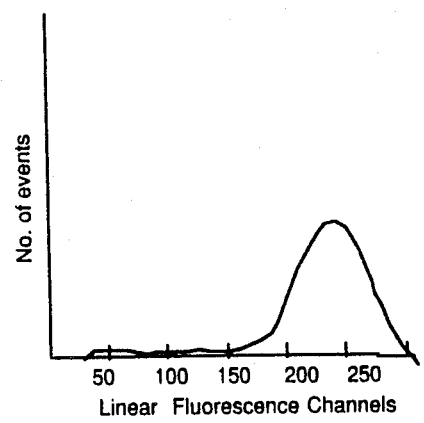
FIG. 6 illustrates the relatively high fluorescence of goat anti mouse bound microbeads labelled with mouse anti human monoclonal antibodies conjugated to FITC, the X and Y coordinates being representative of the same quantities as in FIG. 5.

In another aspect of the invention illustrated by way of example in FIGS. 4-7, there is illustrated a determination of the so-called "effective F/P ratio" of fluorescenated antibody. As schematically illustrated in FIG. 4, the goat anti mouse microbeads produced by the method of FIG. 1 are combined with fluorescent mouse anti human monoclonal antibodies under the conditions of pH 7.2 and time of thirty minutes to produce microbeads with fluorescent mouse anti human monoclonal antibodies attached to goat anti mouse antibodies as further illustrated in FIG. 4. The relatively low fluorescence of the goat anti mouse microbeads is illustrated in FIG. 5 whereas the relatively high fluorescence of the microbead with fluorescent mouse anti human monoclonal antibody attached to the goat anti mouse antibody is illustrated in FIG. 6.

Figure 7:
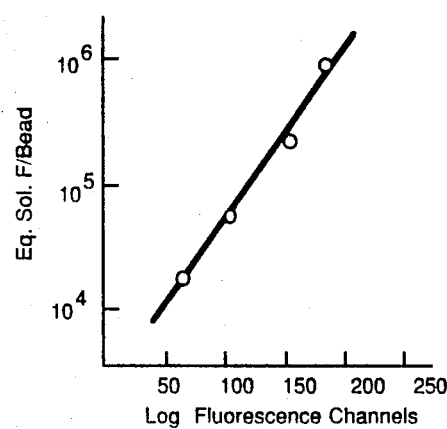
FIG. 7 illustrates a calibration curve utilized for determining the number of equivalent soluble fluorescent dye molecules per microbead according to the invention.

Once the microbead with the fluorescent mouse anti human monoclonal antibody attached to the goat anti mouse antibody has been achieved as in FIG. 4, the number of equivalent soluble fluorescent dye molecules per microbead are next determined against a calibration curve constructed with quantitative fluorescent microbead standards as in FIG. 7 with use of flow cytometry. The number of equivalent soluble fluorescent molecules per microbead as determined with the flow cytometer are then divided by the number of active available goat anti mouse antibody binding sites as determined by the radiolabeling technique illustrated in FIG. 3. The result is the number of equivalent fluorescent molecules per mouse anti human monoclonal antibody, i.e., the effective F/P ratio. The description next turns to more detailed aspects and specific examples of the invention.

Synthesis of the Microbead

Patent and literature references have been given for making large size, uniform microbeads suited to the invention. The synthesis of highly uniform large-sized microbeads (2-20 microns in diameter) is best accomplished according to the invention by swelling seed microbeads sequentially with two or more substances. The swelling is such that, as prescribed by the thermodynamics, the entropy of mixing within the seed microbead allows the seed to swell many times over the amount that the seed would swell with a single substance. The best mode of this synthesis is described in applicant's copending patent applications; Ser. No. 06/685,464 filed Dec. 24, 1984, entitled "Calibration Method for Flow Cytometry Using Fluorescent Microbeads and Synthesis Thereof" and Ser. No. 06/805,654, filed Dec. 11, 1985, entitled "Fluorescent Calibration Microbeads Simulating Stained Cells", the subject matter thereof being incorporated herein by reference.

Method of Covalently Binding Active Biological Molecules

In the synthesis of the microbeads, as described in the two copending patent applications mentioned above, surface epoxy groups are introduced by copolymerization of monomers such as glycidyl methacrylate in with other monomers, e.g., methyl methacrylate. The present invention observes that such epoxy groups are quite stable in aqueous media if the pH is kept close to 7.0 and that the epoxy is an ideal self-reactive group to bind proteinaceous biological molecules. The present invention recognizes that proteins, such as goat anti mouse antibodies, as in FIG. 1, have primary amine groups which will spontaneously form stable amide links with the epoxy groups when the pH is raised to 8.5-10 at room temperature for 6-12 hours or in the cold with longer times being required for binding. The binding is thus carried out under gentle conditions which minimize denaturation of the biological molecules and retain functionality. What has been described is thus the preferred method of the invention for binding biological molecules while retaining their biological functionality, meaning their ability to bind a specific antibody. Other methods deemed suited to the invention for binding active biological molecules include introducing other surface groups, e.g., aldehyde groups which are also self reactive at pH 8-10 with amines forming reducible Schiff's bases, carboxyls which can be activated with water soluble carbodiimides to bind primary amines, and diols which can be activated by cyanogin bromide to bind carboxyls.

Calibration of the Average Number of Functional Binding Sites

The functional binding sites are defined as those covalently bound biological molecules as in FIG. 1 which in turn can bind other specific biological species, e.g., radiolabeled mouse anti human antibodies as in FIG. 3. The average number of functional binding sites is determined by first allowing the microbeads with the functional molecules, e.g., goat anti mouse bound antibodies as in FIG. 1, to react under proper conditions, e.g., at pH 7.2, ionic strength 0.1, and room temperature for 30 minutes, with an excess of radiolabeled target molecules, e.g., mouse anti human monoclonal Leu-3 bound antibodies as in FIG. 3. The microbeads are next washed several times in the same suspension medium to remove all the unbound radiolabeled antibody before the amount of radiolabeled antibody per microbead is determined by standard radiolabel quantitative methods. For example, the specific radioactivity of a known amount of antibody can first be determined and that specific activity used to determine how much antibody was bound to the microbeads in the sample. Then, by determining the number of microbeads with a Hemocytometer or Coulter Counter, the average number of radioactive antibody molecules bound to the microbeads can be determined. This average number is equivalent to the average number of available functional binding sites on the microbead. Once this calibration of average number of available functional binding sites is determined on a sample of the microbeads, the remaining microbeads may be used when binding similar antibodies which are not radioactive, but instead, for example, are fluorescent. It has been observed that neither the radioactivity nor the fluorescence, per se, effect the degree of binding of the target antibody.

Determining the Effective Fluorescent F/P Ratio

Once the number of available functional binding sites have been calibrated as described above, the effective fluorescent F/P ratio can be determined with a flow cytometer. The method is as follows: First, allow the microbeads having the covalently bound biological molecules of FIG. 1 to react with an excess of the fluorescent antibody to be measured as in FIG. 4. After washing, measure the fluorescence of the microbeads with a flow cytometer against a fluorescence calibration curve illustrated in FIG. 7 produced with quantitatively calibrated microbeads which have the same dye and fluorescence spectra as the fluorescent antibody. This determination may be in terms of number of equivalent soluble fluorescent molecules per microbead. Next, divide the number of equivalent soluble fluorescent molecules per microbead by the number of antibodies bound to the microbead by the functional binding sites which is the same as the number of available functional binding sites, as determined above. This gives the effective F/P ratio. This method assumes complete saturation of the available sites and may be tested by using a series of different concentrations of fluorescent antibody.

Microbeads in the size range between 7-10 microns in diameter are especially suited to this task since they are the same size and have about the same number of binding sites as biological cells. This allows the operator of the flow cytometer to do all measurements at about the same instrument settings as are done on biological cells.

Having explained the invention and how microbeads with functional finding sites are achieved, those skilled in the art will appreciate their use, both for screening antibodies and for determining the average number and density of antigen binding sites on biological cells which are next explained by way of exemplary applications of the invention.

Screening Antibodies With Microbeads With Functional Binding Sites

The inhibition methodology used in hemotology and ELISA screening can be applied when using the microbeads with functional binding sites of the invention to screen antibodies and other biological molecules. For example, it is observed that rabbit anti mouse IgM antibody can be covalently bound to the surface of the uniform microbeads and then allowed to react with a new IgM mouse monoclonal antibody which is to be tested. This is followed by reacting the microbeads with FITC conjugated goat anti rabbit antibody. The microbeads are washed well between each step and then run in a flow cytometer. If the microbeads are found to be fluorescent, the test mouse IgM antibody must not have bound, or blocked, the mouse binding sites on the rabbit anti mouse IgM antibodies on the microbead. It then could be concluded that the mouse IgM antibody is not specific. However, if the microbeads are found not to be fluorescent, this indicates high specificity of the mouse IgM antibody because all available rabbit anti mouse IgM sites have been occupied by the test mouse IgM antibody. To complete the method, a control must be run in which the rabbit anti mouse IgM microbeads are reacted directly with the FITC conjugated goat anti rabbit, to ensure that the FITC goat anti rabbit will bind to the microbeads and make the microbeads become fluorescent.

Various specific antigens, e.g., the rabbit anti mouse IgM antibody, can be covalently bound to the described microbeads. This allows the determination of specificity of any number of antibodies with the use of a flow cytometer.

Determining the Average Number and Density of Antigen Binding Sites on Biological Cells Making use of the invention, the method for determining the average number of antigen binding sites on biological cells is as follows: First, determine the effective fluorescent F/P ratio of the antibody to be used as described above. Then "stain" the cells with the fluorescent antibody as normally described by the manufacturer of the antibody. Now measure the average number of fluorescent molecules per cell in terms of equivalent soluble dye molecules per cell against the fluorescent calibration curve (FIG. 7) produced by using the quantitative fluorescent microbead standards, as described above. Divide this number of fluorescent molecules per cell by the effective fluorescent F/P ratio as first determined. The result will be the average number of antibody binding sites per cell.

To determine the average density of antibody binding sites per cell, one must also determine the surface area of the cell. This can be done by calibrating the size channels, i.e., the forward light scatter or the electronic volume, of the flow cytometer and determining the average size of the cells. Assuming that the cells are spherical, as in the case of lymphocytes, the surface area may easily be calculated. This process is described in patent applications Ser. No. 06/685,464 entitled "Calibration Method for Flow Cytometry Using Fluorescent Microbeads and Synthesis Thereof" and Ser. No. 06/805,654 entitled "Fluorescent Calibration Microbeads Simulating Stained Cells" and the previously referred to technical brochure "Quantitative Fluorescein Microbead Standards". Then the average number of antibody binding sites per cell can be divided by the average surface area per cell to give the average number of antibody binding sites per unit area, i.e., the antibody binding density.

The usefulness of the invention is well expressed by recognizing that the knowledge of both the total number and density of antibody binding sites is extremely important to the researcher and clinician when following changes in cellular development or cellular mediated diseases such as Leukemia and AIDS because changes in these numbers can be indicative and act as diagnostic guides to the progression of these conditions.

Further examples relevant to the invention are now given.

EXAMPLE 1

Synthesis of Uniform Microbeads

One milliliter of 1-chlorododecane (CDD) was homogenized with 2.5 ml of 0.25% sodium dodecyl sulfate (SDS) in water and this was added to 5 ml of 10% suspension of 2.02 micron polyvinyl toluene microbeads in 20 ml of SDS solution. Ten milliliters of 30% acetone in water was added to help incorporate the CDD into the microbeads. This was stirred for 12 hours before 1 ml of the suspension was added to 10 ml of distilled water and 20 ml of SDS and evacuated to remove the acetone. One hundred milligrams (1%) of benzoyl peroxide initiator was dissolved in a 10 ml solution of 95% methyl methacrylate and 5% glycidyl methacrylate before it was homogenized with an equal volume of 0.25% SDS solution. Twenty milliliters of the homogenate was then added to the above evacuated suspension of swollen seed microbeads and the suspension was purged with nitrogen and heated to 70° C. for two hours to cause rapid polymerization of the swollen microbeads. The result was a highly uniform microbead with a diameter of 8.3 microns.

EXAMPLE 2

Covalent Binding of Antibodies to Microbeads

The microbeads in Example 1 were washed three times by centrifugation and resuspension with a 0.25% SDS aqueous solution and three times with distilled water to remove the SDS. The microbeads were then suspended in 0.1M NaHCO$_3$ at pH 9.5 One milligram of affinity purified goat anti mouse was rapidly added to five milliliters of microbead suspension of $2 \times 10^6$ microbeads per ml in the carbonate buffer. The suspension mixture was rotated for 6 hours at room temperature then washed six times and stored at 4° C. in a buffer solution containing 0.03 M phosphate, 0.1M NaCl, 0.05% BSA, and 0.05% azide.

EXAMPLE 3

Calibrating the Number of Available Functional Binding Sites

The antibody to be reacted with the microbeads was first labeled with radioactive iodine 131 by mixing it with Iodo-Beads TM (Pierce Chemical Company) and then passed through a G-25 column to remove unbound I-131 as described in the Biorad methodology. The activity of the antibody was determined by measuring the radioactivity of the solution with a gamma counter after it was passed through the G-25 column then determining the protein concentration by spectral absorption at 365 nm. Five micrograms of the radiolabeled antibody were mixed with $4 \times 10^5$ microbeads from Example 2 and allowed to rotate for one hour at room temperature. The microbeads were then washed six times in the pH 7.2 suspension buffer. The activity of the microbeads was then determined with the gamma counter. This number was then divided by the activity per antibody molecule to give the number of antibody molecules which bound per microbead, resulting in $4.5 \times 10^4$ antibodies per microbead. In turn, this value was taken as the same as the number of available functional binding sites per microbead.

EXAMPLE 4

Determination of Effective Fluorescent F/P Ratio

A portion of microbeads, ($2 \times 10^5$) in Example 2 which had been calibrated with radiolabeled antibodies in Example 3 were allowed to react for 30 minutes with an excess (5 μg) of FITC conjugated Leu-3a monoclonal antibody (Becton Dickinson & Co.) suspended in Cold Hanks Balanced Salt Solution (HBSS) containing 5% heat-inactivated fetal calf serum and 0.1% sodium azide. The microbeads were then washed twice with HBSS and resuspended in a phosphate buffer pH 7.2 containing 2% paraformaldehyde. Ten thousand microbeads were then analyzed with a flow cytometer and their fluorescence intensity quantified against a calibration plot produced with quantitative fluorescein microbead standards (Flow Cytometry Standards Corp.). This resulted in a fluorescence of $6.5 \times 10^4$ soluble equivalent fluorescein molecules per microbead. Taking from Example 3 that there were $4.5 \times 10^4$ antibodies bound per microbead and then dividing this into the number of fluorescent molecules per microbead yielded an effective fluorescent F/P ratio of 1.4.

EXAMPLE 5

Determining the Number of Available Antibody Binding Sites Per Cell and the Binding Density Five micrograms of Leu-3a antibody with an effective F/P ratio of 1.4 as determined in Example 4 was reacted with $2 \times 10^5$ purified lymphocytes (purified by Ficoll-Paque® lymphocyte purification density gradient medium (Pharmacia Fine Chemicals)) by the same method as the microbeads described in Example 4. The cells were found to have an average of $1.2 \times 10^5$ equivalent soluble fluorescein molecules per cell as determined against the fluorescence calibration plot. Dividing this fluorescence by the F/P ratio, it indicates that there were an average of $8.6 \times 10^4$ Leu-3a binding sites per labeled cell.

EXAMPLE 6

Determining the Binding Density

The diameter and surface area of the lymphocytes were determined against size calibration plots run on the flow cytometer and found to be 8.6μ in diameter and to have a surface area of 233μ$^2$. This data taken with the average number of Leu-3a binding sites determined in Example 5, indicate that there were an average of 369 binding sites per square micron.

In summary, it can be seen that the simulated cell structure of the invention offers at least these advantages:

(1) By utilizing highly uniform microbeads within a size range of 2–20 microns simulating a range of biological cell size, e.g., platelet to macrophage, and of low coefficient of variation, five percent (5%) or less, uniform results are assured.
(2) Simulates the size of a selected biological cell.
(3) Simulates a selected characteristic of a biological cell, e.g., the specific surface antigen of a cell.
(4) Enables a determination to be made of the effective F/P ratio of an antibody.
(5) Enables a determination to be made of the specificity of an antibody.
(6) Enables a determination to be made of available binding sites per cell.
(7) Enables a determination to be made of the density of the binding sites per cell.
(8) Provides a simulated cell useful in same suspension media as applies to biological cells.
(9) Provides new techniques based on availability of the simulated cell of the invention specifically adapted to flow cytometry or alternatively to fluorescent microscopy.

What is claimed is:

1. A method of determining the effective fluorescence F/P ratio of a fluorescent antibody, comprising:
   (a) providing first microbeads having binding sites capable of binding to the fluorescent antibodies, said microbeads being of known or determinable number of binding sites per microbead;
   (b) providing second calibration microbeads having associated therewith the same fluorescent dye as said fluorescent antibodies, and exhibiting the same fluorescence spectra as said fluorescent antibodies;
   (c) providing a flow cytometer;
   (d) establising a calibration plot for the flow cytometer with said second calibration microbeads, of number of equivalent soluble fluorescent dye molecules per microbead as a function of fluorescence intensity channel of said flow cytometer;
   (e) reacting said first microbeads with excess fluorescent antibodies, to yield fluorescent antibody bound microbeads;
   (f) determining the flourescence intensity channel of said fluorescent antibody-bound microbeads on said flow cytometer;
   (g) for said fluorescence intensity channel determined for said fluorescent antibody-bound microbeads, determining from said calibration plot the number of equivalent soluble fluorescent dye molecules per microbead for said fluorescent antibody-bound microbeads; and
   (h) dividing the number of equivalent soluble fluorescent dye molecules per microbead determined in step (f) by the number of binding sites per microbead, to yield said effective fluorescence F/P ratio of said fluorescent antibody.

2. A method according to claim 1, wherein said first microbeads have a size in the range of from 2 to 20 microns, with a coefficient of variation of 5% or less.

3. A method according to claim 1, wherein said first microbeads have a size in the range of from 7 to 10 microns, with a coefficient of variation of 5% or less.

4. A method according to claim 1, wherein said binding sites are on a protein.

5. A method according to claim 1, wherein said antibody is a monoclonal mouse anti human antibody.

6. A method according to claim 1, wherein said first microbeads have goat anti mouse antibodies covalently bound thereto.

7. A method according to claim 6, wherein said antibody is a monoclonal mouse anti human antibody.

8. A method of determining the average number of binding sites on a biological cell capable of binding to a fluorescent antibody, comprising:
   (a) carrying out the method of claim 1 with first microbeads having substantially the same size as the biological cells to be characterized, thereby determining the effective fluorescence F/P ratio of the fluorescent antibody;
   (b) staining the biological cells with excess said fluorescent antibodies;
   (c) determining the fluorescence intensity channel of said fluorescent antibody-stained cells on said flow cytometer at the same instrument parameters employed to determine effective fluorescence F/P ratio of the fluorescent antibody;
   (d) for said fluorescence intensity channel of said fluorescent antibody-stained cells on said flow cytometer, determining from said calibration plot the number of equivalent soluble fluorescent dye molecules per biological cell; and
   (e) dividing the number of equivalent soluble fluorescent dye molecules per biological cell for said fluorescent antibody-stained cells, by said effective fluorescence F/P ratio determined for said fluorescent antibodies, to yield the average number of binding sites for the fluorescent antibody-stained cells.

9. A method of determining the average density of binding sites on a biological cell capable of binding to a fluorescent antibody, comprising:
   (a) carrying out the method of claim 8 to determine the average number of binding sites for the cell;
   (b) determining the average size of the cell;
   (c) determining the average surface area of the cell; and
   (d) dividing the average number of binding sites per cell determined for said fluorescent anitbody-stained cells, by the average surface area per cell to yield the average number of binding sites per unit area as the density of binding sites for the biological cell.

10. A method of monitoring a cellular state, comprising carrying out the method of claim 9 to determine changes in the total number and average density of binding sites on a biological cell as an indicator of cellular condition.

* * * * *